(12) United States Patent
Liu et al.

(10) Patent No.: US 12,022,864 B2
(45) Date of Patent: Jul. 2, 2024

(54) ULTRASONIC ELECTRONIC CIGARETTE ATOMIZER AND ELECTRONIC CIGARETTE

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Hong Yu, Hunan (CN); Jianhua Yi, Hunan (CN); Yang Wang, Hunan (CN); Yongquan Zhou, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 715 days.

(21) Appl. No.: 16/306,794

(22) PCT Filed: Dec. 17, 2016

(86) PCT No.: PCT/CN2016/110582
§ 371 (c)(1),
(2) Date: Dec. 3, 2018

(87) PCT Pub. No.: WO2017/215221
PCT Pub. Date: Dec. 21, 2017

(65) Prior Publication Data
US 2019/0289914 A1    Sep. 26, 2019

(30) Foreign Application Priority Data

Jun. 15, 2016 (CN) .......................... 201610421230.4
Jun. 16, 2016 (CN) .......................... 201620583532.7

(51) Int. Cl.
*A24F 40/05* (2020.01)
*A24F 40/20* (2020.01)
(Continued)

(52) U.S. Cl.
CPC .............. *A24F 40/05* (2020.01); *A24F 40/20* (2020.01); *A24F 40/40* (2020.01); *A24F 40/42* (2020.01);
(Continued)

(58) Field of Classification Search
CPC ...................................................... A24F 40/05
See application file for complete search history.

(56) References Cited

U.S. PATENT DOCUMENTS 9,731,312 B2 * 8/2017 Hsieh .................. B05B 17/0661
2008/0230052 A1  9/2008 Montaser
(Continued)

FOREIGN PATENT DOCUMENTS

CN    201319860 Y    10/2009
CN    204670383 U    9/2015
(Continued)

OTHER PUBLICATIONS

Miyazaki, Hajime, "Machine translation of JP 2008-104966 A," translated Feb. 13, 2021, Espacenet.com. (Year: 2021).*
(Continued)

*Primary Examiner* — Philip Y Louie
*Assistant Examiner* — Sonny V Nguyen
(74) *Attorney, Agent, or Firm* — MASCHOFF BRENNAN; Ran Pang; Michael Mauriel (57) ABSTRACT

An ultrasonic electronic cigarette atomizer and an electronic cigarette, wherein the ultrasonic electronic cigarette atomizer comprises a shell, a tobacco tar storage bottle, an ultrasonic atomization piece and a flaky tobacco tar storage body fit to one side face of the ultrasonic atomization piece (Continued)

are provided in the shell, and a tobacco tar guide body is fixed to an outer wall of at least one side of the tobacco tar storage bottle; one side face of the tobacco tar guide body is communicated with the inner cavity of the tobacco tar storage bottle, and the other side face of the tobacco tar guide body is contacted with the side face of the tobacco tar storage body which is away from the ultrasonic atomization piece; and the ultrasonic atomization piece and the tobacco tar storage body are provided to be parallel to the length direction of an electronic cigarette.

10 Claims, 8 Drawing Sheets

(51) Int. Cl.
| | | |
|---|---|---|
| *A24F 40/40* | (2020.01) | |
| *A24F 40/42* | (2020.01) | |
| *A24F 40/44* | (2020.01) | |
| *A24F 40/485* | (2020.01) | |
| *B65D 43/02* | (2006.01) | |
| *A24F 40/10* | (2020.01) | |
| *A61M 15/00* | (2006.01) | |
| *B05B 17/06* | (2006.01) | |
| *F16J 15/02* | (2006.01) | |

(52) U.S. Cl.
CPC ............ *A24F 40/44* (2020.01); *A24F 40/485* (2020.01); *B65D 43/022* (2013.01); *A24F 40/10* (2020.01); *A61M 15/001* (2014.02); *A61M 15/0085* (2013.01); *B05B 17/06* (2013.01); *F16J 15/021* (2013.01)

(56) References Cited

U.S. PATENT DOCUMENTS

| | | | | |
|---|---|---|---|---|
| 2014/0150785 | A1* | 6/2014 | Malik | .................. A61M 11/042 |
| | | | | 128/202.21 |
| 2016/0089508 | A1 | 3/2016 | Smith et al. | |
| 2016/0295913 | A1* | 10/2016 | Guo | ........................ A24F 40/05 |
| 2017/0056914 | A1* | 3/2017 | Beaumont | ........... B05B 17/0653 |
| 2018/0296779 | A1* | 10/2018 | Takeuchi | ................ A24F 40/95 |

FOREIGN PATENT DOCUMENTS

| | | | | |
|---|---|---|---|---|
| CN | 205143491 U | | 4/2016 | |
| CN | 105768238 A | | 7/2016 | |
| CN | 105876870 A | | 8/2016 | |
| CN | 205624490 U | | 10/2016 | |
| CN | 205671482 U | | 11/2016 | |
| JP | H0531421 | * | 2/1993 | |
| JP | 2001069963 A | | 3/2001 | |
| JP | 2008104966 A | * | 5/2008 | ............. A24F 40/05 |
| JP | 2010142737 A | * | 7/2010 | |

OTHER PUBLICATIONS

Makoto; Ono; "Machine translation of JP 5-31421," Translated Nov. 17, 2022. (Year: 2022).*

"Machine translation of JP 2010142737," translated Sep. 6, 2023, Clarivate Analytics. (Year: 2023).*

* cited by examiner

ULTRASONIC ELECTRONIC CIGARETTE ATOMIZER AND ELECTRONIC CIGARETTE

CROSS REFERENCE TO RELATED APPLICATIONS

This application is a national phase application of international application number CT/CN2016/110582 filed on Dec. 17, 2016, which claims priority to Chinese application number 201610421230.4 filed on Jun. 15, 2016 and Chinese application number 201620583532.7 filed on Jun. 16, 2016. The entire contents of these applications are hereby incorporated herein by reference.

TECHNICAL FIELD

The present invention belongs to the technical field of electronic cigarettes, and particularly relates to an ultrasonic electronic cigarette atomizer and an electronic cigarette.

BACKGROUND ART

The existing ultrasonic electronic cigarette atomizer comprises a shell and a suction nozzle installed at the top of the shell, a tobacco tar storage device, an ultrasonic atomization piece located below the tobacco tar storage device and a flaky tobacco tar storage body fit to an upper surface of the ultrasonic atomization piece is provided in the shell. The tobacco tar storage device generally only has a tobacco tar bottle body, and the ultrasonic atomization piece and the flaky tobacco tar storage body are both horizontally placed (namely being perpendicular to the length direction of the electronic cigarette). When the existing ultrasonic electronic cigarette atomizer works, it needs to guide tobacco tar onto the tobacco tar storage body from top to bottom by an external tobacco tar guide structure, and heat the tobacco tar by the oscillation of the ultrasonic atomization piece to generate smoke, so that a user obtains smoking experience. However, the existing ultrasonic electronic cigarette atomizer has the following shortcomings:

Firstly, since both of the ultrasonic atomization piece and the flaky tobacco tar storage body are horizontally arranged below the tobacco tar storage device, the tobacco tar is liable to accumulate at the flaky tobacco tar storage body and the ultrasonic atomization piece due to the action of gravity and is liable to generate a tobacco tar submersion phenomenon after long time storage, therefore the smoke can be generated only after longer heating time in use, the atomization start up speed is slow, and the user experience is poor.

Secondly, as the tobacco tar is output from a tobacco tar bottle which has a downward opening by the external tobacco tar guide structure, the tobacco tar is liable to flow out from a gap between the tobacco tar guide structure and the opening of the tobacco tar bottle under the action of gravity, therefore the sealing property of the tobacco tar storage device is poor, and tobacco tar leakage is likely to occur.

Thirdly, a smoke release surface of the tobacco tar storage body is not blocked, the smoke release surface of the tobacco tar storage body is communicated with the suction nozzle directly through an air outlet passage, after the tobacco tar storage body ejects the smoke, the smoke is directly inhaled by the user via the suction nozzle through the air outlet passage, therefore small-granule smoke and large-granule smoke affecting the inhalation taste in the atomized smoke are both sucked into the oral cavity, and thus the overall taste of the smoke is poor.

Contents of Invention

The existing ultrasonic electronic cigarette atomizer is liable to generate a tobacco tar submersion phenomenon, leading to long waiting time for atomization and poor user experience, and tobacco tar leakage is likely to occur. The present invention aims at providing an improved ultrasonic electronic cigarette atomizer and an electronic cigarette in view of the above shortcomings of the prior art, so that no excessive tobacco tar will accumulate on the surface of an ultrasonic atomization piece, the atomization start up speed is high, the sealing property is good, and the tobacco tar is unlikely to leak.

In order to solve the above-mentioned technical problems, the technical solution adopted by the present invention is as follows:

An ultrasonic electronic cigarette atomizer comprises a shell, wherein a tobacco tar storage bottle, an ultrasonic atomization piece and a flaky tobacco tar storage body fit to one side face of the ultrasonic atomization piece are provided in the shell, the ultrasonic electronic cigarette atomizer is structurally characterized in that a tobacco tar guide body is fixed to an outer wall of at least one side of the tobacco tar storage bottle; one side face of the tobacco tar guide body is communicated with the inner cavity of the tobacco tar storage bottle, and the other side face of the tobacco tar guide body is contacted with the side face of the tobacco tar storage body, which is away from the ultrasonic atomization piece; and the ultrasonic atomization piece and the tobacco tar storage body are both provided to be parallel to the length direction of an electronic cigarette.

By means of the above structure, as the ultrasonic atomization piece and the tobacco tar storage body are both provided to be parallel to the length direction of the electronic cigarette, the electronic cigarette is vertically placed when it is not used, therefore the tobacco tar can be prevented from accumulating at the tobacco tar storage body and the ultrasonic atomization piece, and the tobacco tar submersion phenomenon will not appear even the electronic cigarette is placed for a long time, thus smoke can be produced quickly by heating in use, the atomization start up speed is high, and the user experience is good. Meanwhile, as a tobacco tar outlet on the tobacco tar storage bottle is provided in the side face, compared with the tobacco tar storage bottle which has the downward opening in the prior art, the tobacco tar is unlikely to leak in the present invention. The tobacco tar guide body is fixed to the outer side wall of the tobacco tar storage bottle, when the tobacco tar storage bottle is assembled or replaced, the tobacco tar guide body and the tobacco tar storage body can be connected without alignment or other complex actions so as to transfer the tobacco tar, thereby being simple to operate and convenient to use. Furthermore, as the smoke release surface of the tobacco tar storage body is aligned to the tobacco tar guide body, the large-granule smoke released by the tobacco tar storage body during working process of the ultrasonic atomization piece will be impacted back to the tobacco tar guide body so as to be transferred by the tobacco tar guide body to the tobacco tar storage body to be heated and atomized again, the large-granule smoke affecting the inhalation taste is basically filtered in the smoke that is inhaled into the oral cavity, and thus the overall taste of the smoke is good.

Further, the ultrasonic electronic cigarette atomizer further comprises a suction nozzle at the top of the shell, and a vertical vent groove is provided in the surface, away from the tobacco tar storage bottle, of the tobacco tar guide body; the air inlet end of the vertical vent groove is communicated with the outside, and the air outlet end of the vertical vent groove is communicated with the suction nozzle; an accommodation groove which accommodates the tobacco tar guide body is provided in an outer wall of the tobacco tar storage bottle; a tobacco tar seepage hole is provided in the accommodation groove; the accommodation groove is communicated with a groove provided in the outer wall of the tobacco tar storage bottle; and when the tobacco tar guide body is fixed in the accommodation groove, the vertical vent groove is communicated with the groove, and a communication air passage is provided in an outer surface of the tobacco tar storage bottle.

By means of the above structure, the tobacco tar in the tobacco tar storage bottle passes through the tobacco tar seepage hole and is guided by the tobacco tar guide body to the tobacco tar storage cotton and surface of the ultrasonic atomization piece to be atomized, and meanwhile the smoke produced by atomization flows out via the communication air passage, therefore tobacco tar leakage phenomenon caused by an over large contact area between the tobacco tar guide body and the tobacco tar storage body can also be avoided.

Further, one end of the tobacco tar storage bottle is sealed by a tobacco tar bottle plug to conveniently inject the tobacco tar and further guarantee the sealing property of the tobacco tar storage bottle.

Further, a side edge of the tobacco tar bottle plug covers a side edge of the tobacco tar storage bottle, and a notch communicated with the groove is provided in the side edge of the tobacco tar bottle plug at positions corresponding to the groove.

As a preferred implementation, the tobacco tar guide bodies are provided on the outer walls of both sides of the tobacco tar storage bottle.

Further, the ultrasonic electronic cigarette atomizer further comprises a suction nozzle at the top of the shell, and a vertical vent groove is provided in the surface, away from the tobacco tar storage bottle, of the tobacco tar guide body; the air inlet end of the vertical vent groove is communicated with the outside, and the air outlet end of the vertical vent groove is communicated with the suction nozzle; a projection communicated with the inner cavity of the tobacco tar storage bottle is provided on one side of the tobacco tar storage bottle; a tobacco tar bottle plug is provided in the projection; and the tobacco tar guide body is received in a mounting hole in the tobacco tar bottle plug, and the surface, provided with the vertical vent groove, of the tobacco tar guide body, extends out of the tobacco tar bottle plug.

Further, the ultrasonic atomization piece is fixed in an atomization back cover; an electrode bracket is fixed in the atomization back cover on the side, away from the tobacco tar storage bottle, of the ultrasonic atomization piece; an elastic piece electrode is fixed to the electrode bracket, and the elastic piece electrode is in contact with the ultrasonic atomization piece; a first elastic electrode and a second elastic electrode are fixed to the atomization back cover; the first elastic electrode is in contact with the elastic piece electrode; and the second elastic electrode is in contact with the ultrasonic atomization piece.

Further, the side, away from the tobacco tar storage bottle, of the atomization back cover is sealed by an atomization front cover.

Further, the atomization back cover is hermetically connected with the atomization front cover through a first sealing ring.

Further, ultrasonic atomization pieces are provided in the shell on both sides of the tobacco tar storage bottle.

Further, a connecting electrode is fixed in the shell below the tobacco tar storage bottle; a gap is provided between the connecting electrode and the tobacco tar storage bottle; an air inlet hole is provided in the connecting electrode; and the air inlet hole, the gap, the groove in the tobacco tar storage bottle below the tobacco tar guide body, the vertical vent groove in the tobacco tar guide body, the groove in the tobacco tar storage bottle above the tobacco tar guide body and the suction nozzle are communicated successively.

Further, a limiting bracket is fixed in the shell; and the tobacco tar storage bottle is fixed in the limiting bracket, and the surface, provided with the vertical vent groove, of the tobacco tar guide body extends out of the limiting bracket to contact the tobacco tar storage body.

Further, both of the first elastic electrode and the second elastic electrode are in contact with the upper surface of a conductive plate fixed between the limiting bracket and the shell; a vent hole is provided in the conductive plate; a lower surface of the conductive plate is in contact with upper ends of two connecting electrodes fixed to the shell; a gap is provided between the lower surface of the conductive plate and the inner wall of the shell; the vent hole communicates the gap with the vertical vent groove; and the lower end of the connecting electrode extends out of the shell.

Further, the shell on the side, away from the ultrasonic atomization piece, of the tobacco tar storage bottle is sealed by a first side cover; an observation window is provided in the first side cover; and the observation window is communicated with the gap.

Further, the ultrasonic electronic cigarette atomizer further comprises a suction nozzle at the top of the shell, a tobacco tar guide needle fixing base is further provided in the shell, and a hollow tobacco tar guide needle is provided on the tobacco tar guide needle fixing base; a tobacco tar outlet hole is provided in the tobacco tar storage bottle; a sealing cover capable of being pierced by the tobacco tar guide needle is provided at the tobacco tar outlet hole of the tobacco tar storage bottle, and the sealing cover blocks the tobacco tar outlet hole; the tobacco tar guide needle is inserted into the inner cavity of the tobacco tar storage bottle from the sealing cover; a tobacco tar outlet end of the tobacco tar guide needle is contacted with the tobacco tar guide body; an air inlet hole is provided in the lower part of the shell, and an airflow passage is provided among the interior of the shell, the air inlet hole and the suction nozzle; and a conductor capable of conducting the ultrasonic atomization piece to the power supply is further provided in the shell.

By means of the above structure, when the tobacco tar storage bottle is inserted into the shell, the tobacco tar guide needle pierces the sealing cover to enable the tobacco tar to flow onto the tobacco tar guide body along the hollow cavity of the tobacco tar guide needle. By means of cooperation of the tobacco tar guide needle and the sealing cover, sealability between the tobacco tar guide needle and the sealing cover is enhanced, and tobacco tar leakage is avoided. The tobacco tar flowing out of the tobacco tar guide needle is absorbed by the tobacco tar guide body, and the tobacco tar guide body transfers the tobacco tar onto the ultrasonic atomization piece for atomization thereby. Due to the low temperature property of the ultrasonic atomization piece, the atomization temperature is relatively low, the temperature generally does not exceed 170 degrees Celsius, and no scorched flavor or odor is produced.

Further, the tobacco tar storage bottle is detachably connected with the shell, a first hollow cavity which places the tobacco tar storage bottle is provided on one side in the shell, and a first side cover which packages the tobacco tar storage bottle is provided. The first side cover is in magnetic connection or buckled connection with the shell.

In a further improved solution, the tobacco tar storage bottle can be made into a disposable device and can be replaced after being used. Due to the independent tobacco tar storage bottle, the tobacco tar is longer in shelf life and is cleaner and more sanitary.

Further, a spring is provided between the side wall of the tobacco tar storage bottle and the tobacco tar guide needle fixing base, and after the tobacco tar storage bottle is packaged in the shell, the spring is compressed.

The tobacco tar storage bottle is elastically abuts against the tobacco tar guide needle fixing base to facilitate replacement of the tobacco tar storage bottle.

Further, the conductor comprises a third elastic electrode contacted with the side face of the ultrasonic atomization piece which is away from the tobacco tar storage body, and a connecting electrode connected with the third elastic electrode through a conducting wire, the connecting electrode is provided at the bottom of the shell, and the other end of the connecting electrode is detachably connected with an external power supply.

Further, the ultrasonic electronic cigarette atomizer further comprises an atomization piece fixing base and an electrode fixing base, and the ultrasonic atomization piece and the tobacco tar storage body are vertically installed on the atomization piece fixing base together; an electrode mounting hole is provided in the electrode fixing base, and the third elastic electrode is fixed to the electrode mounting hole; and the atomization piece fixing base is connected with the electrode fixing base.

In the above solution, the ultrasonic atomization piece and the tobacco tar storage body are vertically installed together for the purpose that after the tobacco tar is transferred to the tobacco tar storage body, the tobacco tar will not excessively humidify the tobacco tar storage body under the action of the gravity, and thus the situation that the amount of smoke of the first puff is small will not happen.

Further, the ultrasonic atomization piece and the electrode fixing base are detachably connected with the shell, a second hollow cavity is provided on the side, opposite to the tobacco tar storage bottle, in the shell and a second side cover which seals the second hollow cavity is provided. The second side cover and the wall of the second hollow cavity are sealed by a sealing ring.

Further, a horizontal vent groove is provided in the tobacco tar guide needle fixing base, the tobacco tar guide body is fixedly installed on the tobacco tar guide needle fixing base, and a vertical vent groove is provided in the tobacco tar guide body; the horizontal vent groove is communicated with the vertical vent groove to form a first airflow passage; and a gap is provided between the tobacco tar storage body and the tobacco tar guide needle fixing base, the gap is communicated with the first airflow passage, and an airflow passes through the first airflow passage and the gap and finally rises to the suction nozzle.

Further, the tobacco tar guide body is columnar, and the tobacco tar guide body penetrates through the hollow cavity of the tobacco tar guide needle and extends into the inner cavity of the tobacco tar storage bottle.

To facilitate cleaning of suction nozzle of the electronic cigarette, the shell is detachably connected with the suction nozzle.

Based on the same inventive concept, the present invention further provides an ultrasonic electronic cigarette adopting the ultrasonic electronic cigarette atomizer.

Compared with the prior art, no excessive tobacco tar is accumulated on the surface of the ultrasonic atomization piece in the present invention, the problem that the oversaturated tobacco tar storage body is hard to be heated and atomized is solved, the atomization start up speed is high, the taste of the smoke is good, the sealing property is good, the tobacco tar is unlikely to leak, and the ultrasonic electronic cigarette atomizer is clean and sanitary and is convenient to install and detach.

REFERENCE SIGNS

1. tobacco tar storage bottle, 2. tobacco tar guide body, 3. vertical vent groove, 4. accommodation groove, 5. tobacco tar seepage hole, 6. groove, 7. tobacco tar bottle plug, 8. notch, 9. projection, 10. mounting hole, 11. shell, 12. ultrasonic atomization piece, 13. suction nozzle, 14. tobacco tar storage body, 15. atomization back cover, 16. electrode bracket, 17. elastic piece electrode, 18. first elastic electrode, 19. second elastic electrode, 20. atomization front cover, 21. external thread, 22. connecting electrode, 23. gap, 24. limiting bracket, 25. gap, 26. conductive plate, 27. vent hole, 28. observation window, 29. first sealing ring, 30. tobacco tar pass hole, 31. air inlet hole, 32. insulating ring, 33. mounting boss, 34. mounting through hole, 35. mounting projection, 36. mounting hole, 37. connecting projection, 38. mounting notch, 39. suction nozzle mounting hole, 40. first side cover, 41. tobacco tar guide needle, 42. horizontal vent groove, 43. tobacco tar outlet hole, 44. tobacco tar guide needle fixing base, 45. sealing cover, 46. spring, 47. third elastic electrode, 48. atomization piece fixing base, 49. electrode fixing base, 50. second side cover, 51. first airflow passage, 52. second sealing ring, and 53. fixing groove.

SPECIFIC MODE FOR CARRYING OUT THE INVENTION

Embodiment 1

Figure 1:
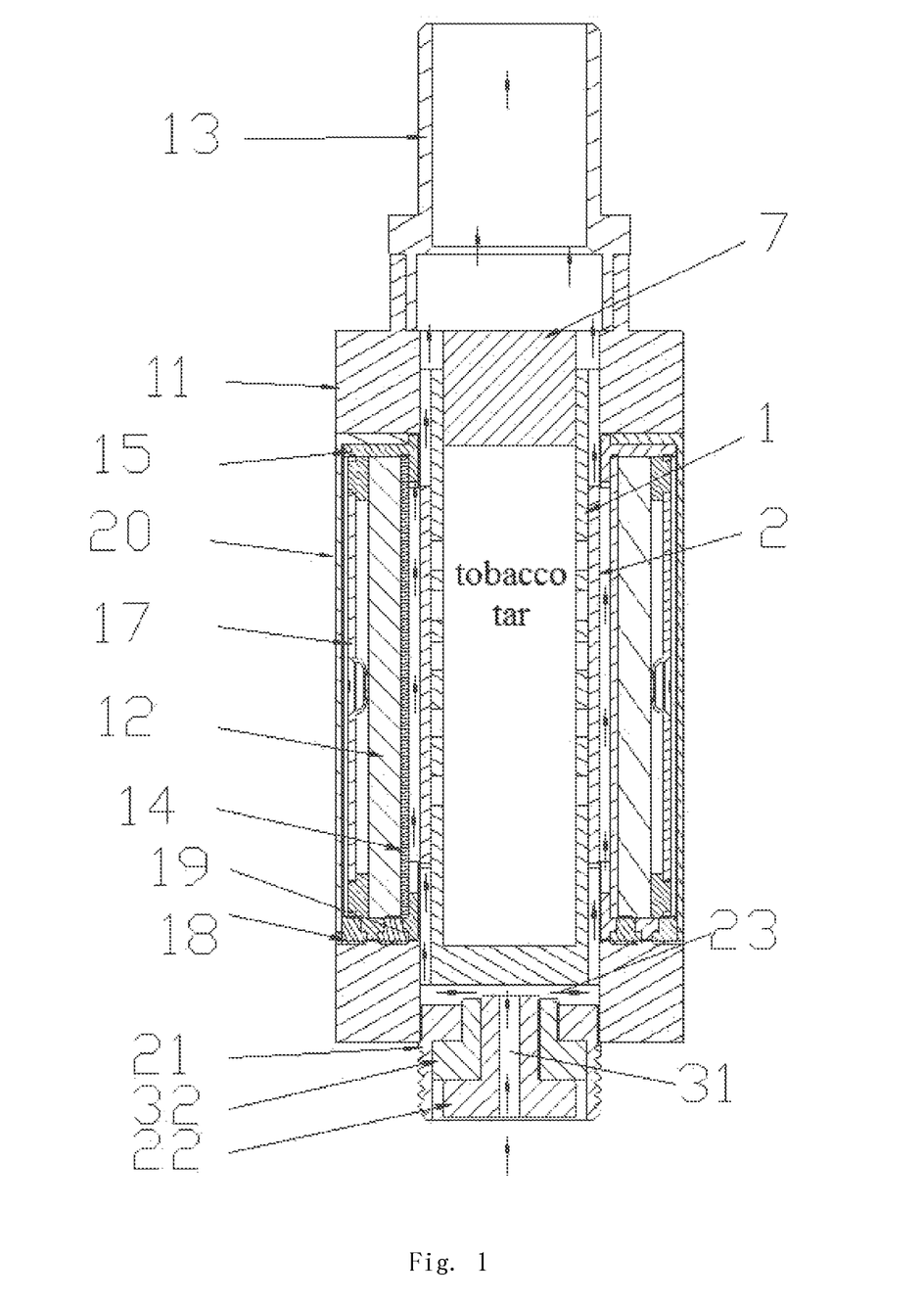
FIG. 1 is a section view of an atomizer of embodiment 1.
Figure 2:
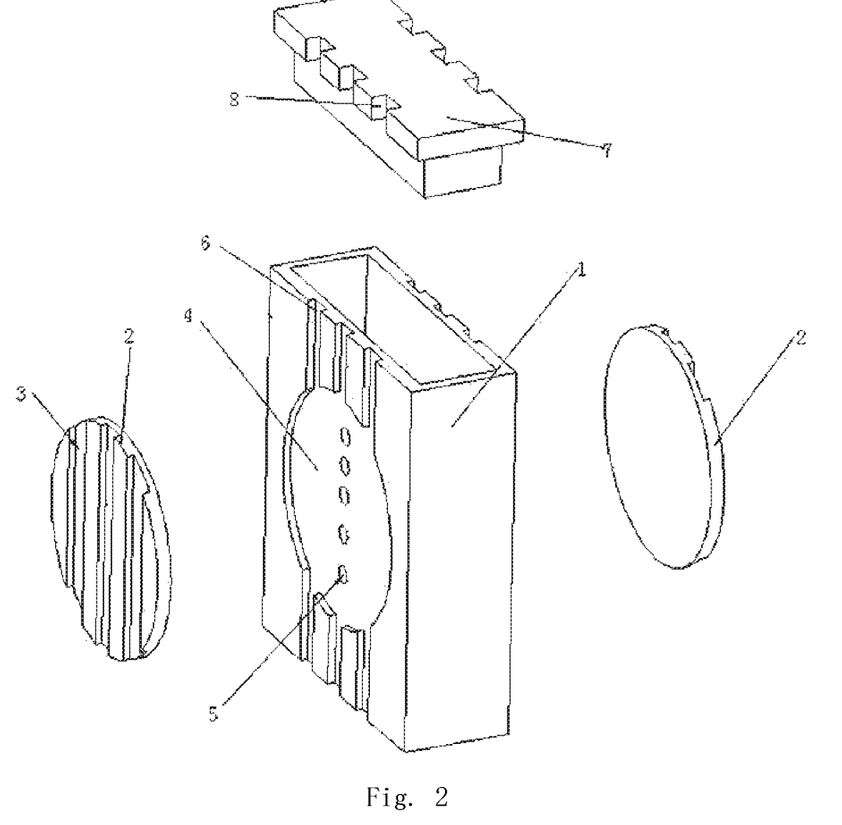
FIG. 2 is an exploded view of a tobacco tar storage bottle in FIG. 1.
Figure 3:
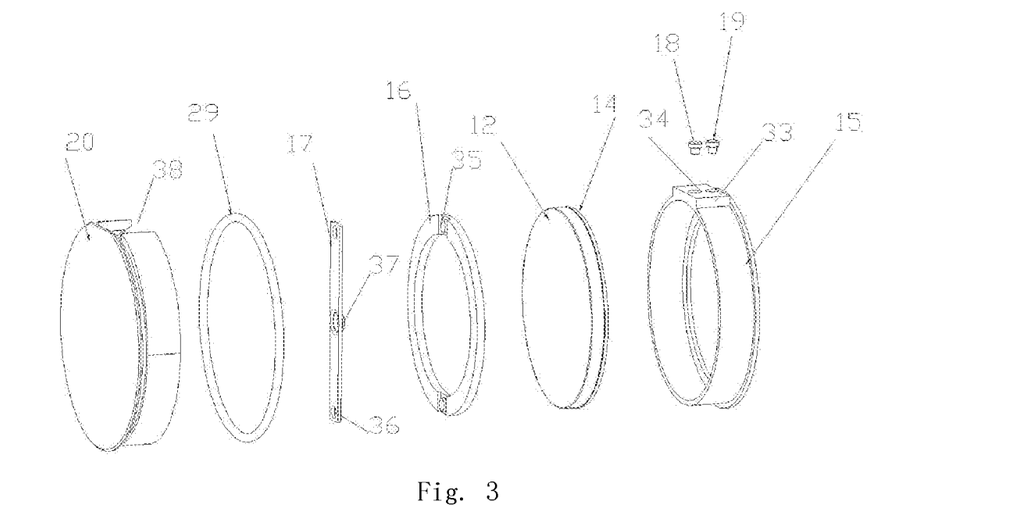
FIG. 3 is a partial exploded view at an ultrasonic atomization piece in FIG. 1.

As shown in FIG. 1 to FIG. 3, an ultrasonic electronic cigarette atomizer in an electronic cigarette of the present invention comprises a shell 11, a tobacco tar storage bottle 1, an ultrasonic atomization piece 12 and a flaky tobacco tar storage body 14 fit to one side face of the ultrasonic atomization piece 12 are provided in the shell 11, and tobacco tar guide bodies 2 are fixed to outer walls of both sides of the tobacco tar storage bottle 1; one side face of the tobacco tar guide body 2 is communicated with the inner cavity of the tobacco tar storage bottle 1, and the other side face of the tobacco tar guide body 2 is contacted with the side face of the tobacco tar storage body 14 which is away from the ultrasonic atomization piece 12; and the ultrasonic atomization piece 12 and the tobacco tar storage body 14 are provided to be parallel to the length direction of the electronic cigarette. The inner cavity of the tobacco tar storage bottle 1 is used for storing tobacco tar.

The electronic cigarette atomizer further comprises a suction nozzle 13 at the top of the shell 11, and a vertical vent groove 3 is provided in the surface, away from the tobacco tar storage bottle 1, of the tobacco tar guide body 2; the air inlet end of the vertical vent groove 3 is communicated with the outside, and the air outlet end of the vertical vent groove 3 is communicated with the suction nozzle 13; an accommodation groove 4 which accommodates the tobacco tar guide body 2 is provided in an outer wall of the tobacco tar storage bottle 1; a tobacco tar seepage hole 5 is provided in the accommodation groove 4; and the accommodation groove 4 is communicated with a groove 6 provided in the outer wall of the tobacco tar storage bottle 1. The tobacco tar guide body 2 can be integrally provided with the shell 11 and can also be embedded in the accommodation groove 4. In the embodiment, the tobacco tar guide body 2 is circular, the accommodation groove 4 is also circular correspondingly, and the outside diameter of the tobacco tar guide body 2 is matched with the inside diameter of the accommodation groove 4. When the tobacco tar guide body 2 is fixed in the accommodation groove 4, the vertical vent groove 3 is communicated with the groove 6, and a communication air passage is provided in an outer surface of the tobacco tar storage bottle 1, namely, an axial communication air passage (i.e., an air passage parallel to the axial line of the tobacco tar storage bottle 1) which runs through the surface of the tobacco tar storage bottle 1, so that the gas is discharged from the communication air passage, and a tobacco tar leakage phenomenon can be prevented.

One end of the tobacco tar storage bottle 1 is sealed by a tobacco tar bottle plug 7 to conveniently inject the tobacco tar. When the tobacco tar needs to be added, the tobacco tar can be injected by opening the tobacco tar bottle plug 7.

In embodiment 1, the tobacco tar bottle plug 7 comprises an end face whose shape and size are matched with those of an upper end of the tobacco tar storage bottle 1, a lower surface (the surface close to the tobacco tar storage bottle 1) of the end face is connected with a connecting part, and the shape and size of the connecting part are matched with those of an opening on the tobacco tar storage bottle 1. A side edge of the tobacco tar bottle plug 7 covers a side edge of the tobacco tar storage bottle 1, and a notch 8 communicated with the groove 6 is provided in the side edge at positions, corresponding to the groove 6, of the tobacco tar bottle plug 7, so that the gas which passes through the communication air passage is smoothly discharged from the notch 8.

The tobacco tar guide bodies 2 are provided on the outer walls of both sides of the tobacco tar storage bottle 1, and both sides of the tobacco tar storage bottle 1 can guide the tobacco tar.

The ultrasonic atomization piece 12 is fixed in an atomization back cover 15; an electrode bracket 16 is fixed in the atomization back cover 15 on the side, away from the tobacco tar storage bottle 1, of the ultrasonic atomization piece 12; an elastic piece electrode 17 is fixed to the electrode bracket 16, and the elastic piece electrode 17 is in contact with the ultrasonic atomization piece 12; a first elastic electrode 18 and a second elastic electrode 19 are fixed to the atomization back cover 15; the first elastic electrode 18 is in contact with the elastic piece electrode 17; and the second elastic electrode 19 is in contact with the ultrasonic atomization piece 12.

In the present invention, the ultrasonic atomization piece 12 is a solid piezoelectric ceramic piece, both surfaces of the piezoelectric ceramic piece are coated with conducting layers, and the two conducting layers are in contact with a positive electrode and a negative electrode respectively and can generate high frequency oscillation after being electrified.

A mounting boss 33 is provided on the outer wall of the atomization back cover 15, two mounting through holes 34 are provided in the mounting boss 33, and the first elastic electrode 18 and the second elastic electrode 19 are respectively fixed in the two mounting through holes 34.

The electrode bracket 16 is in the shape of a circular ring, mounting projections 35 are provided on the circular ring, mounting holes 36 are provided in both ends of the elastic piece electrode 17, and during installation, the two mounting projections 35 on corresponding positions of the circular ring respectively project into the two mounting holes 36. A connecting projection 37 is provided on the surface, facing the ultrasonic atomization piece 12, of the elastic piece electrode 17, and the connecting projection 37 is in contact with the surface of the ultrasonic atomization piece 12.

The connecting projection 37 and the second elastic electrode 19 are respectively in contact with the positive electrode and the negative electrode of the ultrasonic atomization piece 12, and can make the ultrasonic atomization piece 12 to oscillate once being electrified.

A mounting notch 38 is provided in a position on an atomization front cover 20 corresponding to the mounting boss 33 on the atomization back cover 15 so as to facilitate the connection of the atomization front cover 20 and the atomization back cover 15.

In order to prevent tobacco tar leakage of the atomizer and guarantee a good-looking appearance, the side, away from the tobacco tar storage bottle 1, of the atomization back cover 15 is sealed by the atomization front cover 20.

The atomization back cover 15 is hermetically connected with the atomization front cover 20 through a first sealing ring 29 so as to further prevent tobacco tar leakage of the atomizer and guarantee a more compact and stable internal structure.

Ultrasonic atomization pieces 12 are provided in the shell 11 on both sides of the tobacco tar storage bottle 1, therefore the atomization efficiency can be improved, and the requirements of large smoke amount can be satisfied.

A connecting electrode 22 is fixed in the shell 11 below the tobacco tar storage bottle 1; a gap 23 is provided between the connecting electrode 22 and the tobacco tar storage bottle 1; an air inlet hole 31 is provided in the connecting electrode 22; and the air inlet hole 31, the gap 22, the groove 6 in the tobacco tar storage bottle 1 below the tobacco tar guide body 2, the vertical vent groove 3 in the tobacco tar guide body 2, the groove 6 in the tobacco tar storage bottle 1 above the tobacco tar guide body 2 and the suction nozzle 13 are communicated successively to form an airflow passage of the atomizer. The connecting electrode 22 and the shell 11 are insulated by an insulating ring 32, external threads 21 are provided on the outer wall of the insulating ring 32, and the external threads 21 are matched with internal threads on the shell 11, thereby ensuring convenient installation and detachment.

The structures on both sides of the tobacco tar storage bottle 1 are symmetrical, and thus the structure of the atomizer is more beautiful.

The tobacco tar storage bottle 1 and the ultrasonic atomization piece 12, etc. are detachable, thereby being convenient to assemble and maintain.

Embodiment 2

Figure 4:
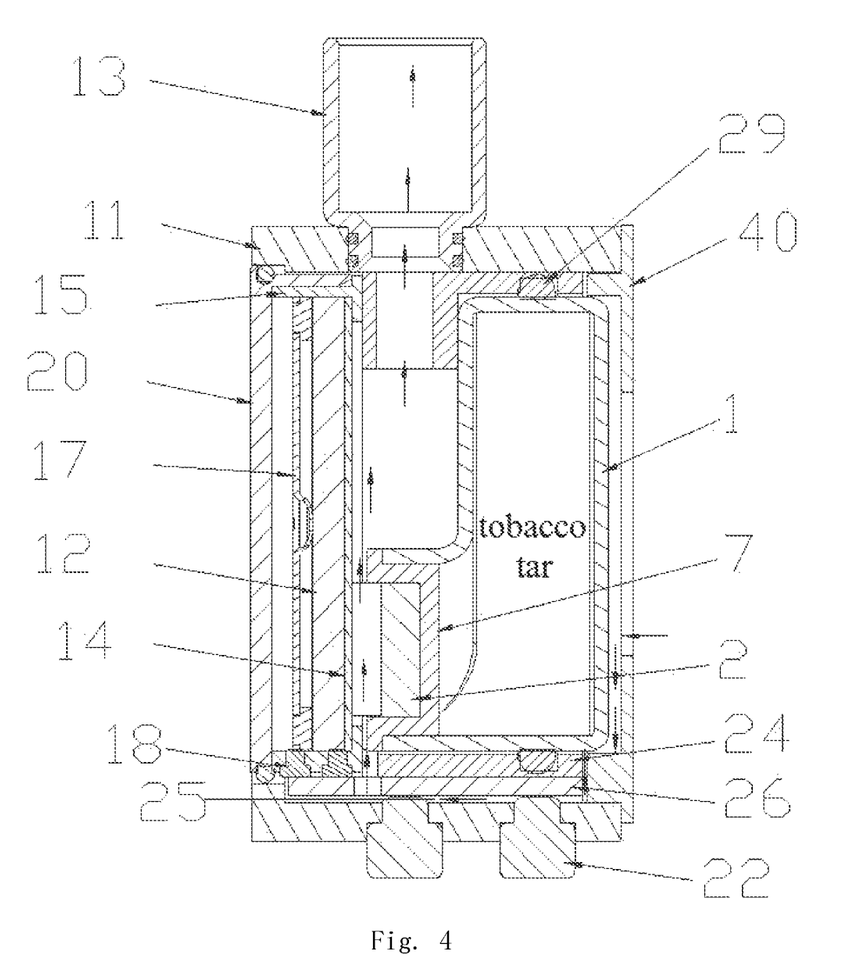
FIG. 4 is a section view of an atomizer of embodiment 2.
Figure 5:
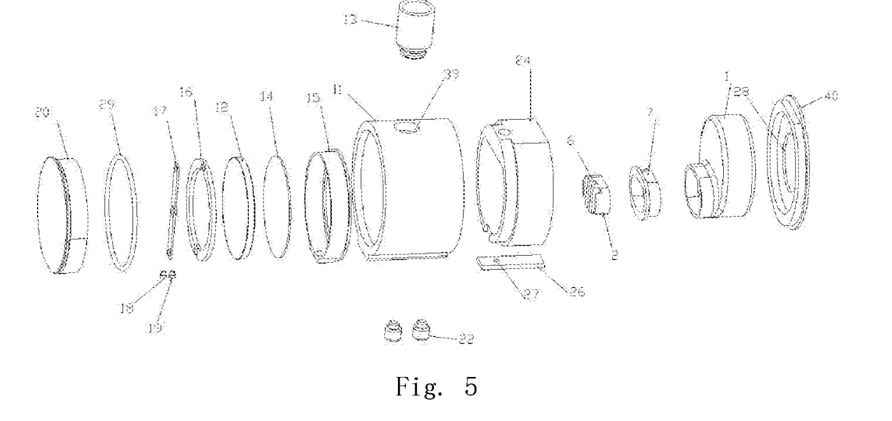
FIG. 5 is an exploded view of FIG. 4.
Figure 6:
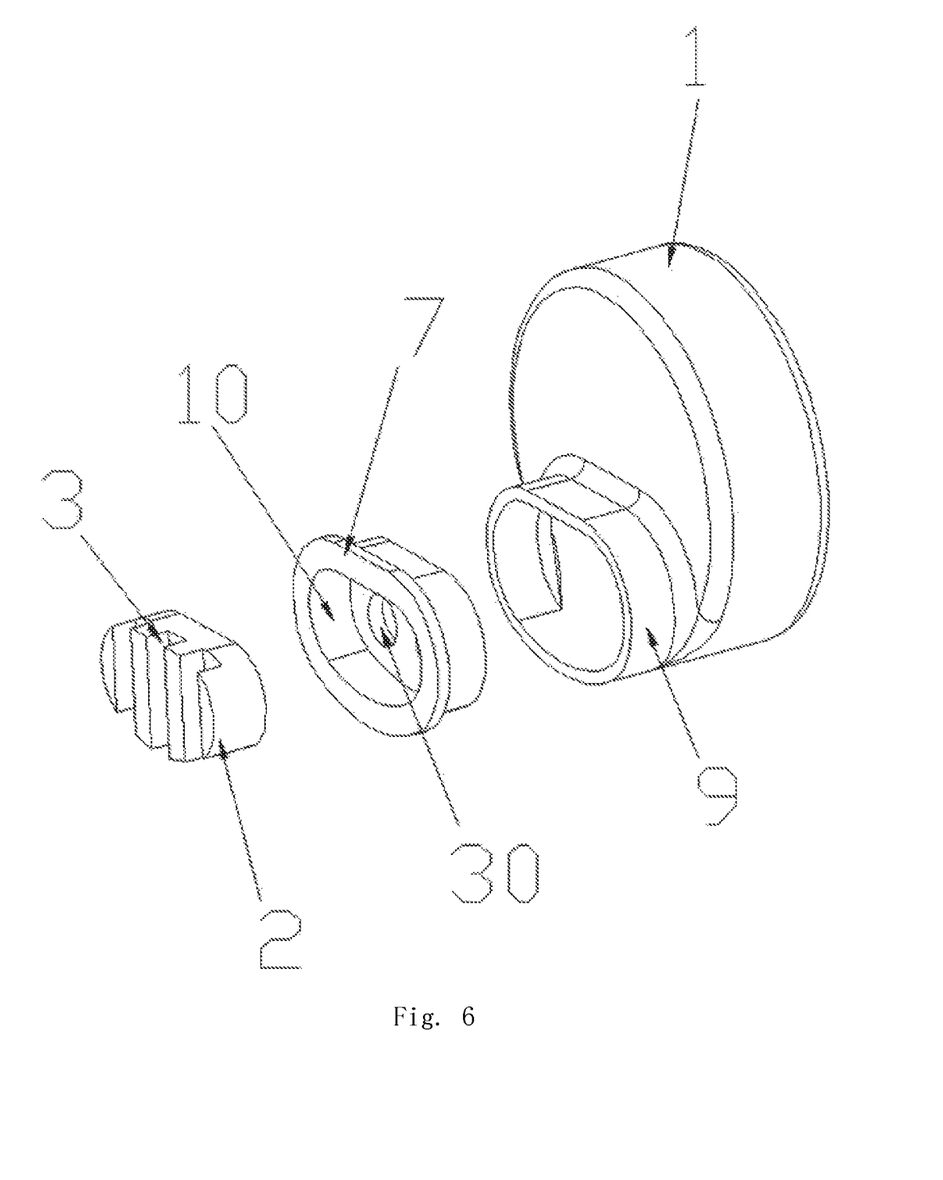
FIG. 6 is an exploded view of a tobacco tar storage bottle in FIG. 4.

FIG. 4 to FIG. 6 show the structure of the ultrasonic electronic cigarette atomizer in the electronic cigarette of embodiment 2 of the present invention, the embodiment 2 is similar to the embodiment 1, the difference between embodiment 1 and embodiment 2 lies in that a projection 9 communicated with the inner cavity of the tobacco tar storage bottle 1 is provided on one side of the tobacco tar storage bottle 1; a tobacco tar bottle plug 7 is provided in the projection 9; and the tobacco tar guide body 2 is received in a mounting hole 10 in the tobacco tar bottle plug 7, and the surface, provided with the vertical vent groove 3, of the tobacco tar guide body 2 extends out of the tobacco tar bottle plug 7. A tobacco tar pass hole 30 is provided in the tobacco tar bottle plug 7, and when the tobacco tar guide body 2 is received in the mounting hole 10, the tobacco tar guide body is communicated with the inner cavity of the tobacco tar storage bottle 1 through the tobacco tar pass hole 30. The tobacco tar flows into the tobacco tar guide body 2 through the tobacco tar pass hole 30.

In embodiment 2, the tobacco tar storage bottle 1 is a cylinder, the projection 9 is provided on a bottom surface of the cylinder, the tobacco tar guide body 2 is blocky tobacco tar guide cotton or the tobacco tar guide body 2 and the tobacco tar bottle plug 7 are integrally provided, namely being integrated, therefore the structure is simple, and the production cost is low.

A limiting bracket 24 is fixed in the shell 11; and the tobacco tar storage bottle 1 is fixed in the limiting bracket 24, and the surface, provided with the vertical vent groove 3, of the tobacco tar guide body 2 extends out of the limiting bracket 24 to contact the tobacco tar storage body 14. The limiting bracket 24 functions to fix the tobacco tar storage bottle 1 so as to prevent the tobacco tar storage bottle 1 from moving after being mounted and guarantee good contact between the tobacco tar guide body 2 and the tobacco tar storage body 14.

Both of the first elastic electrode 18 and the second elastic electrode 19 are in contact with the upper surface of a conductive plate 26 fixed between the limiting bracket 24 and the shell 11; a vent hole 27 is provided in the conductive plate 26; the lower surface of the conductive plate 26 is in contact with upper ends of two connecting electrodes 22 fixed to the shell 11; a gap 25 is provided between the lower surface of the conductive plate 26 and the inner wall of the shell 11; the vent hole 27 communicates the gap 25 with the vertical vent groove 6; and the lower end of the connecting electrode 22 extends out of the shell 11. The conductive plate 26 can guarantee a good internal electrical connection of the atomizer. The two connecting electrodes 22 can be respectively in contact with the positive electrode and the negative electrode of the battery and are respectively conducted to the first elastic electrode 18 and the second elastic electrode 19 through the conductive plate 26.

The conductive plate 26 can be a PCB, and thus the cost is low.

The shell 11 on the side, away from the ultrasonic atomization piece 12, of the tobacco tar storage bottle 1 is sealed by a first side cover 40; an observation window 28 is provided in the first side cover 40; and the observation window 28 is communicated with the gap 25. The observation window 28, the gap 25, the vent hole 27, the vent groove 6 and the suction nozzle 13 are communicated successively to form an airflow passage. The condition of the tobacco tar in the tobacco tar storage device can be observed through the observation window so as to conveniently judge whether the tobacco tar needs to be added, and the observation window can also be used as an air inlet of the airflow passage, so that the structure is simple and beautiful.

As shown in FIG. 6, the shell 1 of the atomizer in the embodiment is a cylinder with two open ends, a suction nozzle mounting hole 39 is provided in the side wall of the cylinder, and the bottom end of the suction nozzle 13 is in screw joint with the inner wall of the mounting hole 39, thereby being convenient to detach and replace or clean.

Embodiment 3

Figure 7:
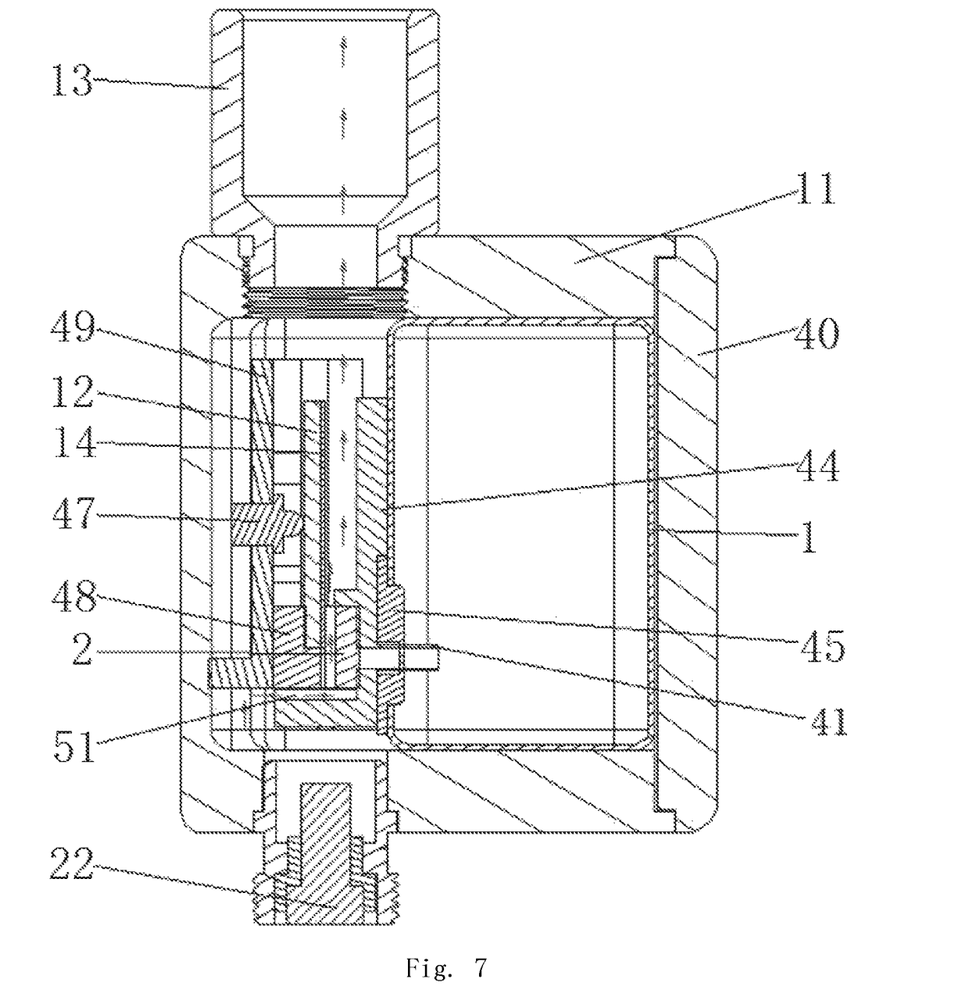
FIG. 7 is a section view of an atomizer of embodiment 3.
Figure 8:
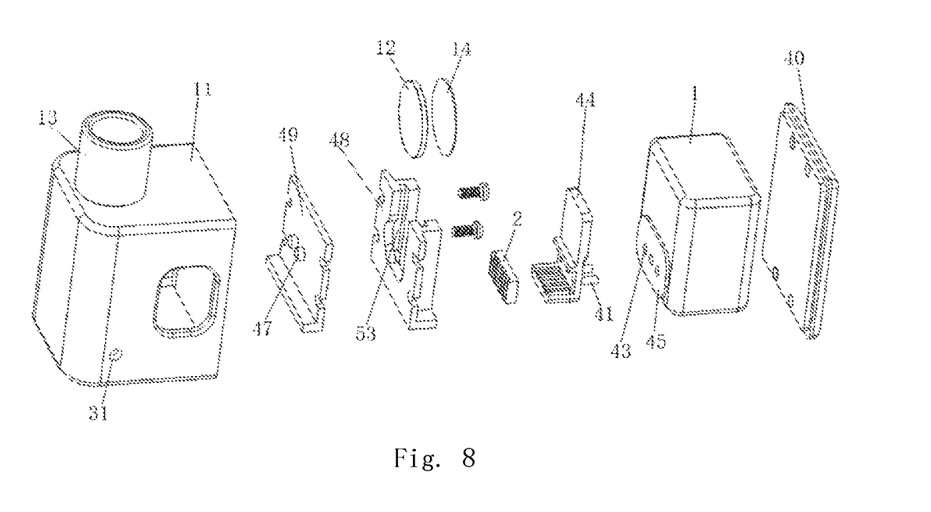
FIG. 8 is an exploded view of FIG. 7.
Figure 9:
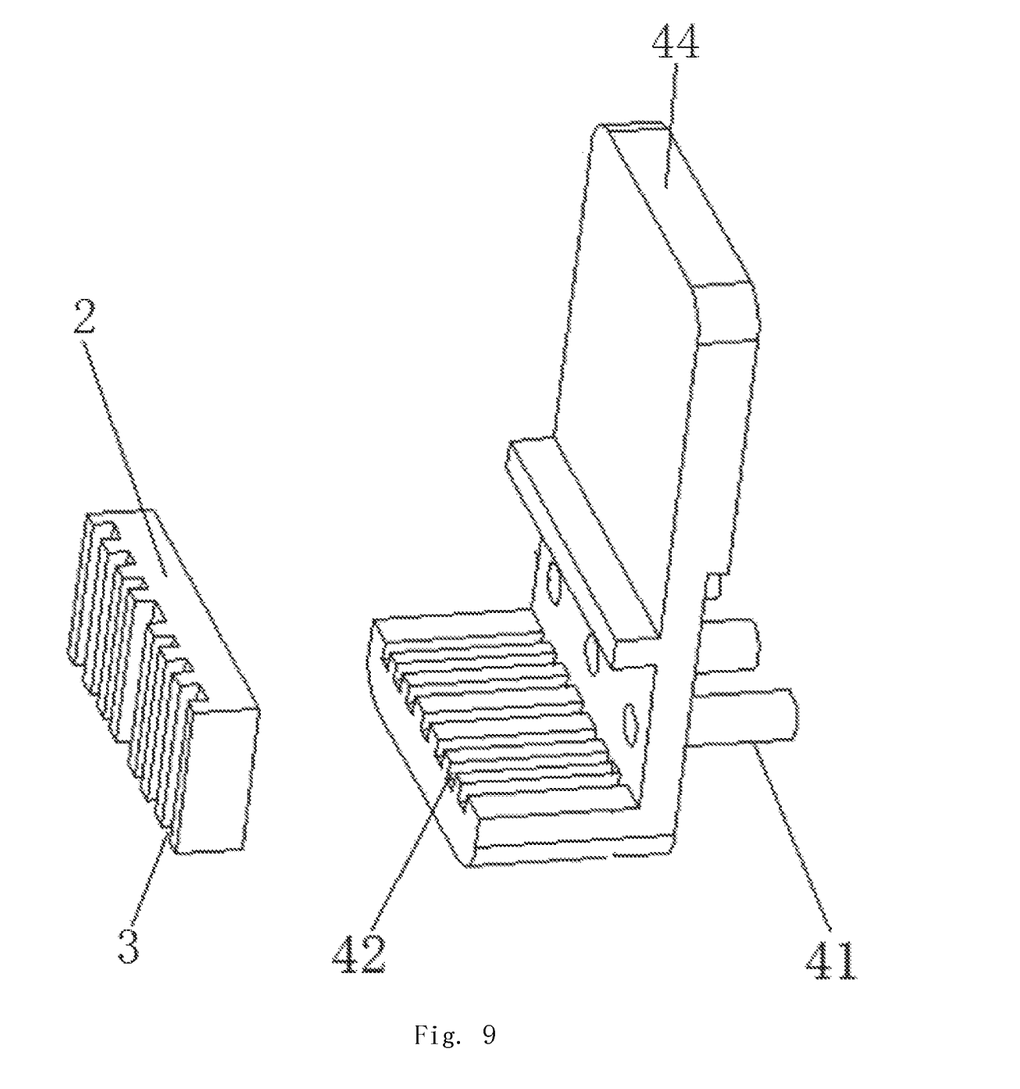
FIG. 9 is a structural schematic diagram of a tobacco tar guide needle fixing base and a tobacco tar guide body in FIG. 7.

As shown in FIG. 7 to FIG. 9, an ultrasonic electronic cigarette atomization core in an electronic cigarette of embodiment 3 of the present invention comprises a shell 11, a tobacco tar storage bottle 1, an ultrasonic atomization piece 12 and a flaky tobacco tar storage body 14 fit to one side face of the ultrasonic atomization piece 12 are provided in the shell 11, wherein a tobacco tar guide body 2 is fixed to an outer wall of at least one side of the tobacco tar storage bottle 1; one side face of the tobacco tar guide body 2 is communicated with the inner cavity of the tobacco tar storage bottle 1, and the other side face of the tobacco tar guide body 2 is contacted with the side face of the tobacco tar storage body 14 which is away from the ultrasonic atomization piece 12; and the ultrasonic atomization piece 12 and the tobacco tar storage body 14 are provided to be parallel to the length direction of the electronic cigarette.

The atomizer further comprises a suction nozzle 13 at the top of the shell 11, and a tobacco tar guide needle fixing base 44 is further provided in the shell 11, and a hollow tobacco tar guide needle 41 is provided on the tobacco tar guide needle fixing base 44; a tobacco tar outlet hole 43 is provided in the tobacco tar storage bottle 1; a sealing cover 45 capable of being pierced by the tobacco tar guide needle 41 is provided at the tobacco tar outlet hole 43 of the tobacco tar storage bottle 1, and the sealing cover 45 blocks the tobacco tar outlet hole 43; the tobacco tar guide needle 41 is inserted into the inner cavity of the tobacco tar storage bottle 1 from the sealing cover 45; a tobacco tar outlet end of the tobacco tar guide needle 41 is contacted with the tobacco tar guide body 2; an air inlet hole 31 is provided in the lower part of the shell 11, and an airflow passage is provided among the interior of the shell 11, the air inlet hole 31 and the suction nozzle 13; and a conductor capable of conducting the ultrasonic atomization piece 12 to the power supply is further provided in the shell 11. The sealing cover 45 is preferably made of silica gel.

The tobacco tar storage bottle 1 is detachably connected with the shell 11, a first hollow cavity which places the tobacco tar storage bottle 1 is provided on one side in the shell 11, and a first side cover 40 which packages the tobacco tar storage bottle 1 is provided.

The conductor comprises a third elastic electrode 47 contacted with the side face of the ultrasonic atomization piece 12 which is away from the tobacco tar storage body 14, and a connecting electrode 22 connected with the third elastic electrode 47 through a conducting wire, the connecting electrode 22 is provided at the bottom of the shell 11, and the other end of the connecting electrode 22 is detachably connected with an external power supply.

The atomizer further comprises an atomization piece fixing base 48 and an electrode fixing base 49, and the ultrasonic atomization piece 12 and the tobacco tar storage body 14 are vertically installed on the atomization piece fixing base 48 together; an electrode mounting hole is provided in the electrode fixing base 49, and the third elastic electrode 47 is fixed to the electrode mounting hole; and the atomization piece fixing base 48 is connected with the electrode fixing base 49.

A horizontal vent groove 42 is provided in the tobacco tar guide needle fixing base 44, the tobacco tar guide body 2 is fixedly installed on the tobacco tar guide needle fixing base 44, and a vertical vent groove 3 is provided in the tobacco tar guide body 2; the horizontal vent groove 42 is communicated with the vertical vent groove 3 to form a first airflow passage 51; and a gap is provided between the tobacco tar storage body 14 and the tobacco tar guide needle fixing base 44, the gap is communicated with the first airflow passage 51, and airflow passes through the first airflow passage 51 and the gap and finally rises to the suction nozzle 13.

Embodiment 4

Figure 10:
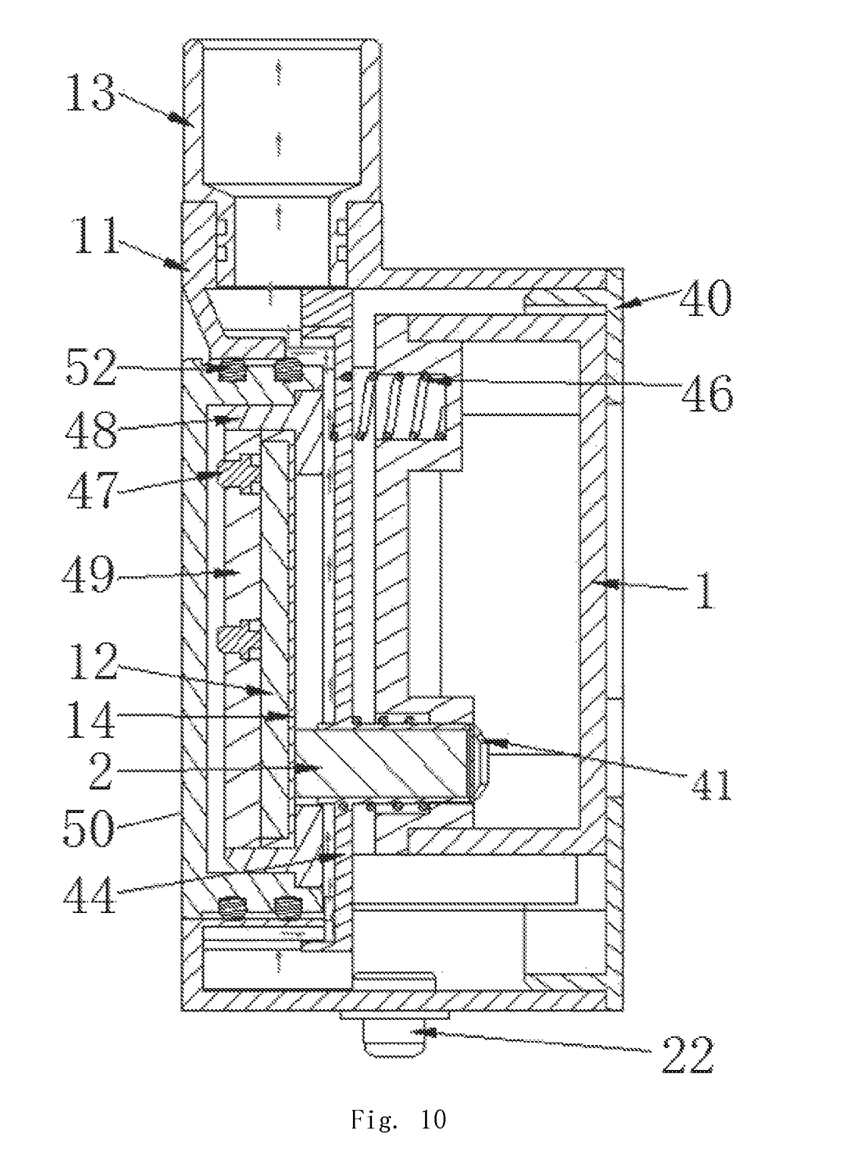
FIG. 10 is a section view of an atomizer of embodiment 4.

FIG. 10 shows the structure of the ultrasonic electronic cigarette atomizer in the electronic cigarette of embodiment 4 of the present invention, the embodiment 4 is similar to the embodiment 3, the difference between embodiment 4 and embodiment 3 lies in that the ultrasonic atomization piece 12 and the electrode fixing base 49 are detachably connected with the shell 11, a second hollow cavity is provided on the side, opposite to the tobacco tar storage bottle 1, in the shell 11, and a second side cover 50 which seals the second hollow cavity is provided. The second side cover 50 and the wall of the second hollow cavity are sealed by a sealing ring 52.

The tobacco tar guide body 2 is columnar, and the tobacco tar guide body 2 penetrates through the hollow cavity of the tobacco tar guide needle 41 and extends into the inner cavity of the tobacco tar storage bottle 1.

A spring 46 is provided between the side wall of the tobacco tar storage bottle 1 and the tobacco tar guide needle fixing base 44, and after the tobacco tar storage bottle 1 is packaged in the shell 11, the spring 46 is compressed. After the tobacco tar in the tobacco tar storage bottle 1 is used up, the first side cover 40 is opened, and the tobacco tar storage bottle 1 is pushed out by the spring 46, so that the user can conveniently replace the tobacco tar storage bottle 1.

Although the embodiments of the present invention have been described above in combination with the drawings, the present invention is not limited to the specific embodiments described above, and the specific embodiments described above are merely illustrative and are not restrictive, those of ordinary skill in the art can also make a lot of forms under the enlightenment of the present invention without departing from the purpose of the present invention or the protection scope of the claims, and all these forms fall within the protection scope of the present invention.

The invention claimed is:

1. An ultrasonic electronic cigarette atomizer, comprising a shell, a tobacco tar storage bottle, an ultrasonic atomization piece and a sheet-like tobacco tar storage body comprising a side face covering one side face of the ultrasonic atomization piece are provided in the shell; wherein:
   a tobacco tar guide body is fixed to an outer wall of at least one side of the tobacco tar storage bottle, and a tobacco tar seepage hole is provided in a side face of the tobacco tar storage bottle;
   one side face of the tobacco tar guide body is communicated with an inner cavity of the tobacco tar storage bottle through the tobacco tar seepage hole, and another side face of the tobacco tar guide body, opposite to the side face of the tobacco tar guide body, is in contact with another side face of the tobacco tar storage body opposite to the side face of the tobacco tar storage body covering the ultrasonic atomization piece;
   the ultrasonic atomization piece and the tobacco tar storage body are provided to be parallel to the length direction of an electronic cigarette; and
   the tobacco tar storage body is composed of tobacco tar storage cotton;
   the ultrasonic electronic cigarette atomizer further comprising a suction nozzle at the top of the shell, wherein:
   a vertical vent groove is provided in the another side face, opposite to the tobacco tar storage bottle, of the tobacco tar guide body;
   an air inlet end of the vertical vent groove is communicated with the outside, and an air outlet end of the vertical vent groove is communicated with the suction nozzle;
   an accommodation groove which accommodates the tobacco tar guide body is provided in an outer wall of the tobacco tar storage bottle;
   the tobacco tar seepage hole is provided in the accommodation groove;
   the accommodation groove is communicated with a groove provided in the outer wall of the tobacco tar storage bottle; and
   when the tobacco tar guide body is embedded in the accommodation groove, the vertical vent groove is communicated with the groove, and a communication air passage is provided in an outer surface of the tobacco tar storage bottle.

2. The ultrasonic electronic cigarette atomizer of claim 1, wherein one end of the tobacco tar storage bottle is sealed by a tobacco tar bottle plug.

3. The ultrasonic electronic cigarette atomizer of claim 2, wherein a side edge of the tobacco tar bottle plug covers a side edge of the tobacco tar storage bottle, and a notch communicated with the groove is provided in the side edge of the tobacco tar bottle plug at positions corresponding to the groove.

4. The ultrasonic electronic cigarette atomizer of claim 3, wherein the tobacco tar guide body is a first tobacco guide body, further comprising:
   a second tobacco tar guide body, wherein the first and second tobacco tar guide bodies are provided on the outer walls of respective sides of the tobacco tar storage bottle.

5. The ultrasonic electronic cigarette atomizer of claim 4, wherein ultrasonic atomization pieces are provided in the shell on both sides of the tobacco tar storage bottle.

6. The ultrasonic electronic cigarette atomizer of claim 1, wherein the ultrasonic atomization piece is fixed in an atomization back cover; an electrode bracket is fixed in the atomization back cover on the side, away from the tobacco tar storage bottle, of the ultrasonic atomization piece; an elastic piece electrode is fixed to the electrode bracket, and the elastic piece electrode is in contact with the ultrasonic atomization piece; a first elastic electrode and a second elastic electrode are fixed to the atomization back cover; the first elastic electrode is in contact with the elastic piece electrode; and the second elastic electrode is in contact with the ultrasonic atomization piece.

7. The ultrasonic electronic cigarette atomizer of claim 6, wherein the side, away from the tobacco tar storage bottle, of the atomization back cover is sealed by an atomization front cover.

8. The ultrasonic electronic cigarette atomizer of claim 7, wherein the atomization back cover is hermetically connected with the atomization front cover through a first sealing ring.

9. The ultrasonic electronic cigarette atomizer of claim 1, wherein:
- a connecting electrode is fixed in the shell below the tobacco tar storage bottle;
- a gap is provided between the connecting electrode and the tobacco tar storage bottle;
- an air inlet hole is provided in the connecting electrode; and
- the air inlet hole, the gap, a first portion of the groove in the tobacco tar storage bottle below the tobacco tar guide body, the vertical vent groove in the tobacco tar guide body, a second portion of the groove in the tobacco tar storage bottle above the tobacco tar guide body and the suction nozzle are communicated successively.

10. An ultrasonic electronic cigarette, wherein:
the ultrasonic electronic cigarette comprises an ultrasonic electronic cigarette atomizer comprising a shell, a tobacco tar storage bottle, an ultrasonic atomization piece and a sheet-like tobacco tar storage body comprising a side face covering one side face of the ultrasonic atomization piece are provided in the shell; wherein:
- a tobacco tar guide body is fixed to an outer wall of at least one side of the tobacco tar storage bottle, and a tobacco tar seepage hole is provided in a side face of the tobacco tar storage bottle;
- one side face of the tobacco tar guide body is communicated with an inner cavity of the tobacco tar storage bottle through the tobacco tar seepage hole, and another side face of the tobacco tar guide body, opposite to the side face of the tobacco tar guide body, is in contact with another side face of the tobacco tar storage body opposite to the side face of the tobacco tar storage body covering the ultrasonic atomization piece;
- the ultrasonic atomization piece and the tobacco tar storage body are provided to be parallel to the length direction of the electronic cigarette; and
- the tobacco tar storage body is composed of tobacco tar storage cotton;

the ultrasonic electronic cigarette atomizer further comprising a suction nozzle at the top of the shell, wherein:
- a vertical vent groove is provided in the another side face, opposite to the tobacco tar storage bottle, of the tobacco tar guide body;
- an air inlet end of the vertical vent groove is communicated with the outside, and an air outlet end of the vertical vent groove is communicated with the suction nozzle;
- an accommodation groove which accommodates the tobacco tar guide body is provided in an outer wall of the tobacco tar storage bottle;
- the tobacco tar seepage hole is provided in the accommodation groove;
- the accommodation groove is communicated with a groove provided in the outer wall of the tobacco tar storage bottle; and
- when the tobacco tar guide body is embedded in the accommodation groove, the vertical vent groove is communicated with the groove, and a communication air passage is provided in an outer surface of the tobacco tar storage bottle.

\* \* \* \* \*